(12) United States Patent
Driscoll, Sr.

(10) Patent No.: US 6,699,489 B1
(45) Date of Patent: Mar. 2, 2004

(54) ECOLOGICALLY BENIGN PRODUCT FOR FIRE ANT CONTROL

(76) Inventor: Richard Edward Driscoll, Sr., 225 Rambling Loop, Weatherford, TX (US) 76087-7657

( * ) Notice: Subject to any disclaimer, the term of this patent is extended or adjusted under 35 U.S.C. 154(b) by 18 days.

(21) Appl. No.: 09/962,982

(22) Filed: Sep. 26, 2001

Related U.S. Application Data

(60) Provisional application No. 60/286,817, filed on Apr. 26, 2001.

(51) Int. Cl.$^7$ .................. A01N 25/00; A61K 31/715
(52) U.S. Cl. ............................. 424/405; 514/54
(58) Field of Search .............................. 424/405; 514/54

(56) References Cited

FOREIGN PATENT DOCUMENTS

| GB | 1462443 | * | 1/1977 |
| GB | 2050170 | * | 1/1981 |

* cited by examiner

Primary Examiner—Alton N. Pryor
(74) Attorney, Agent, or Firm—Stanley H. Zeyher

(57) ABSTRACT

A fire ant pesticide consisting of a liquid derived from a solution of water and animal waste; oil, molasses, and a surfactant.

2 Claims, 2 Drawing Sheets

ECOLOGICALLY BENIGN PRODUCT FOR FIRE ANT CONTROL

This invention is based on Provisional Application entitled "Ecologically Benign Method for Fire Ant Control" filed Apr. 26, 2001, application Ser. No. 60/286,817 and claims the priority filing date of that application.

FIELD OF INVENTION

This invention relates to an ecologically benign product which has for its primary focus the control and eradication of fire ants, and in particular the eradication of fire ants of the species solenopsis invicta.

BACKGROUND OF THE INVENTION

There has long been a need to control the spread of fire ants. At present they have invaded ever-increasing areas of the Southeastern and Southwestern United States and the Western Coast of California. It has been estimated that the red imported fire ant causes more than three hundred million dollars worth of damage per year in Texas alone. This damage is in addition to the greater and even more widespread menace the fire ant poses to the safety of humans, animals and other forms of wildlife.

Fire ants are omnivorous, feeding on almost any plant or animal matter. In rural habitats fire ants have a major impact on ground nesting animals from insects to reptiles, to birds to mammals. The arrival of the fire ant into an ecosystem wrecks havoc on the local ecological community. In some instances, the depredation caused by fire ants has completely eliminated some species from an ecosystem with resulting adverse repercussions throughout the local food chain.

One approach, which has been employed to control the fire ant with minimal success, involves the use of chemicals, a treatment which itself often imposes environmental hazards. Moreover the fire ant develops immunity to chemicals through biological change rendering such treatment both costly and often ineffective.

BRIEF DESCRIPTION OF THE DRAWINGS

For the purpose of best illustrating the invention there is shown in the drawings a flow chart and diagrammatic diagram of a preferred process for producing a key component of the pesticidal concentrate comprising this invention; it being understood, however, that this invention is not limited to the precise arrangements and instrumentalities shown for the production of that component.

DETAILED DESCRIPTION OF THE INVENTION

Figure 1:
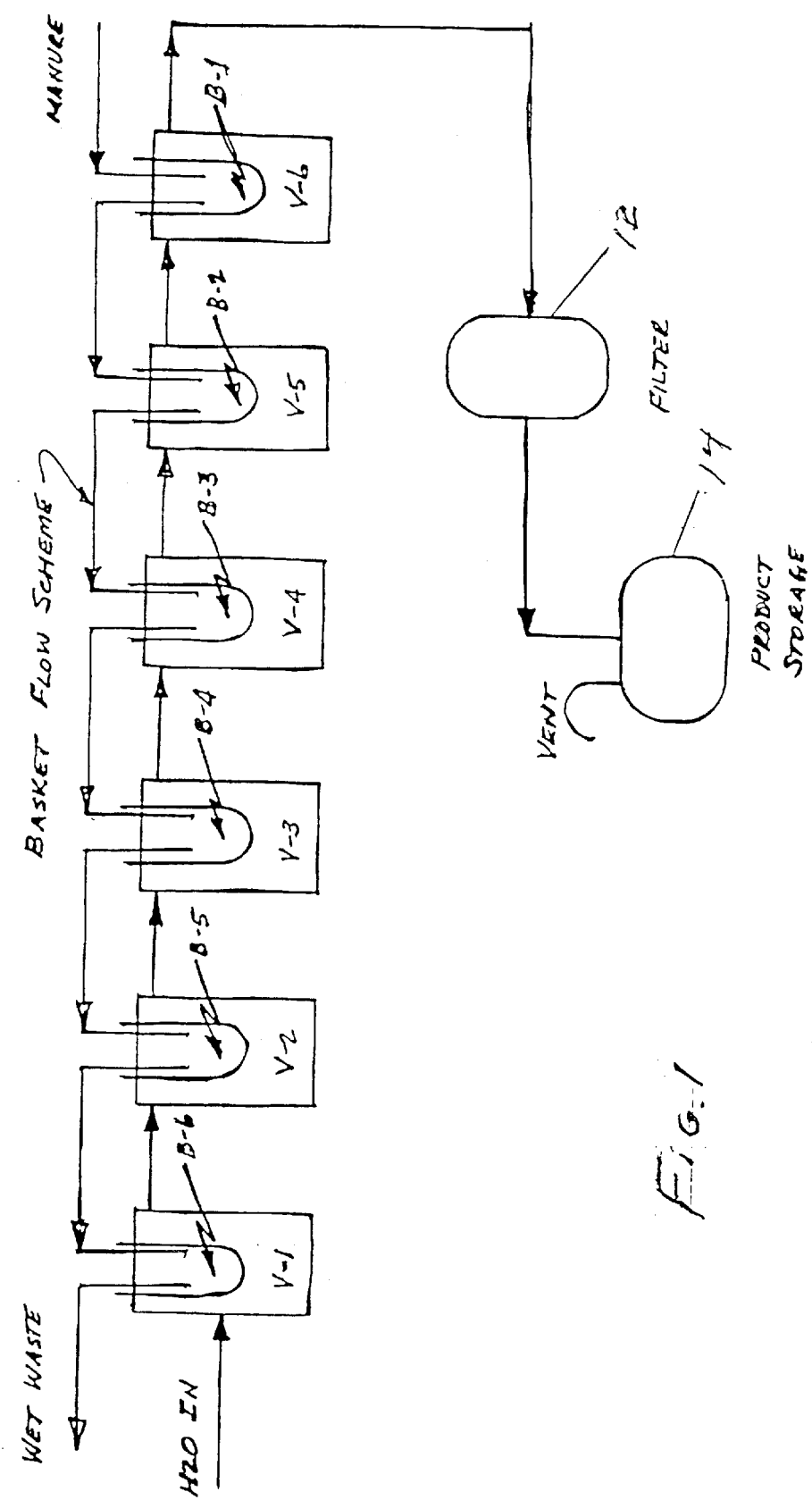
FIG. 1 is a block flow diagram of a process for producing extract liquor, a key component of the fire ant control product comprising the present invention.

The present invention avoids the previously mentioned problems by use of a unique combination of components which both individually and in combination are environmentally benign but when used in the manner to be described are lethal to the fire ant. I have discovered, through extensive experimentation, a product which will both eradicate the fire ant, leaving behind after its application to the fire ant mound, a residue which is not only environmentally benign but is beneficial to both the soil and its microbial population.

The product of this invention is a four component concentrate which when applied to the fire ant mound in the manner to be described, results in eradication of the fire ant. The concentrate consists of an extract obtained from a solution of water and animal waste, hereinafter referred to as "extract liquor"; an oil, as hereinafter defined; molasses; and a surfactant. The preferred formulation of the concentrate and the specification of each of its components are set out below.

The extract liquor is a concoction prepared by the careful digestion of certain selected herbivorous animal manure submerged in a water bath. One method of preparing the liquor is to take a 5 to 10 gallon capacity plastic bucket and put one or two gallons of fresh horse manure in the bottom of the bucket and cover it with water to within about an inch of the top of the bucket. The bucket is then loosely covered and allowed to sit at ambient temperature. The concoction is periodically agitated to insure that all the manure is contacted with water. When the system temperature is above 60 degrees Fahrenheit gas generation occurs. In a start up sequence for the manufacture of extract liquor the initial generation time is a minimum of about four weeks when the average temperature is about 60 degrees F. After this period of time, in a system of four five-gallon buckets, one can gather one gallon of extract from each bucket, a product rate of one gallon of extract liquor per week per bucket. The buckets are then recharged with fresh water and the system is allowed to "digest" for another week. The cycle is then repeated. After about five or six cycles of remove and recharge about one-half a gallon of fresh manure must be added to the system to provide feed for the microorganisms in the system. There is no prolonged waiting period after recharging with fresh manure. The digestion/extraction takes place under conditions that are not totally aerobic or anaerobic. Any surface encrustation which occurs is broken up by mild agitation. The extract liquor thus formed is dark brown to black in color, not transparent, and free of suspended solids. As noted this process of decant and refill over a four week cycle can be repeated for a period of three to four months or until gas evolution begins to fall off indicating a decrease in microbial activity. When this occurs it is necessary to add more fresh manure. When this is done microbial activity increases and the decanting and refilling operation can continue. If the system temperature drops to about forty degrees Fahrenheit or below, gas generation substantially ceases. At this point the production of extract liquor ceases. Due to seasonal variations in manure quality, system temperature variations and other variables the insecticidal value of the extract liquor produced in this manner was found to vary widely. Although this procedure produces viable product when properly monitored as to the parameters of operation and the quality of manure employed, a further and more elaborate process for large scale production is set out below.

Figure 2:
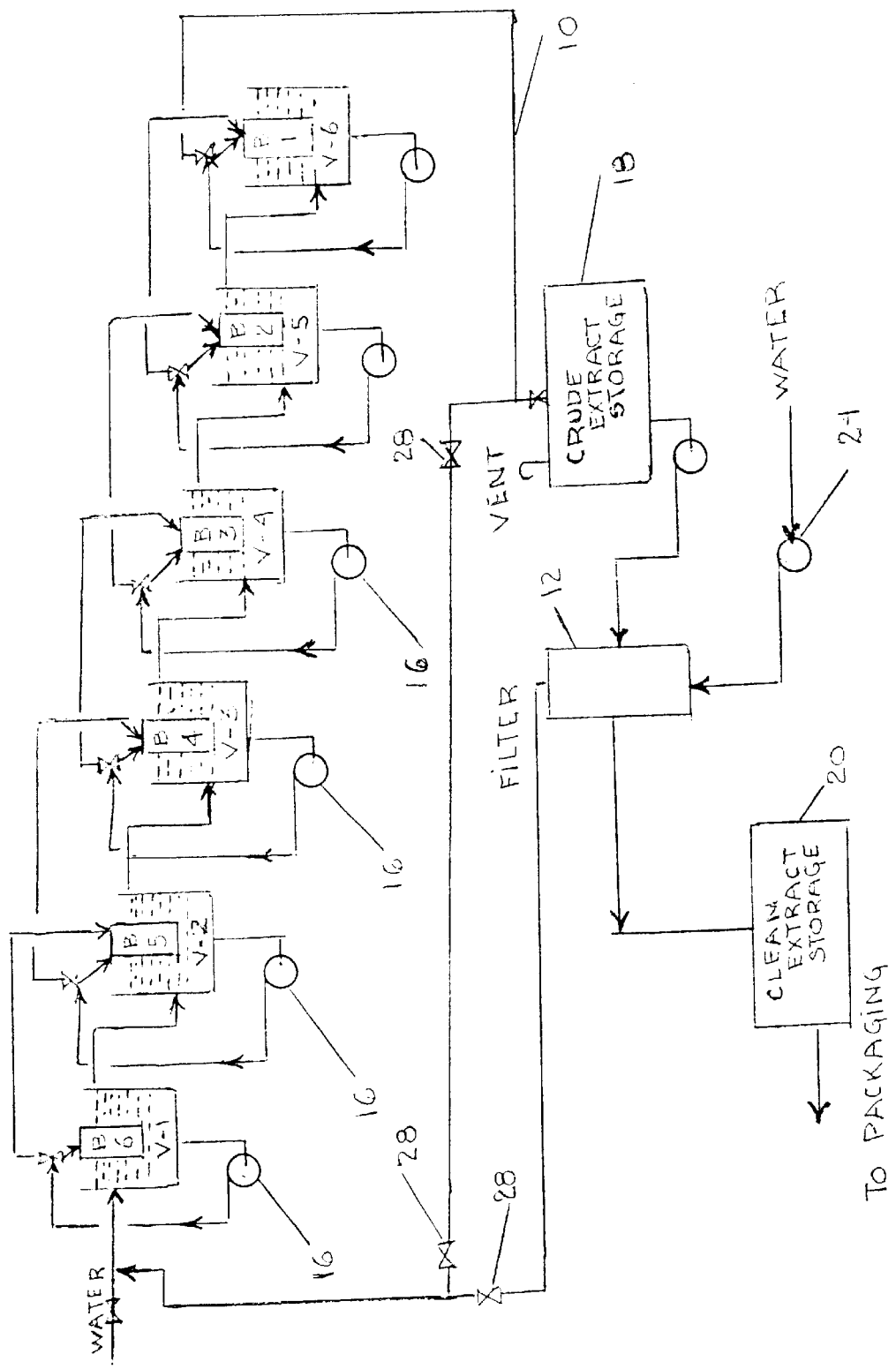
FIG. 2 is a schematic, depicting the mechanical elements making up the process illustrated in FIG. 1.

A more controlled process than the one discussed in the immediately proceeding paragraph is depicted in the flow chart shown in FIG. 1. Referring to that figure water vessels are indicated as V-1 through V-6. Manure-holding baskets are designated as B-1 through B-6. The baskets are arranged so that they can be easily submerged in, and lifted out of, the water vessels and allowed to drain completely before moving from one vessel to the next. Basket B-1 proceeds in timed increments down the line until it is sequentially submerged in each succeeding vessel from V-6 to V-1. After removal of basket B-1 from vessel V-6 basket B-1 is allowed to drain and the residual spent manure is removed and placed in a pile for the production of compost. This final compost can be applied to any portion of the yard or flower bed. The normal sequence of operation is to move the baskets forward from one vessel to the next at weekly intervals. To initiate operation the vessels, which for purposes of illustration are of 50 to 75 gallon capacity, are filled with water. Water from vessel V-6 is returned to vessel V-1 through a recirculation loop 10, as seen in FIG. 2. The rate of recirculation of water in the closed system is on the order of 1 to 5 gallons per minute. Basket B-1 is next charged with animal manure, preferably horse manure, using about 10 to 15 gallons of manure. The basket cover is closed and the basket is submerged in vessel V-6. One week later basket B-1 is lifted from vessel V-6, allowed to drain and moved to vessel V-5 where it is again submerged. Meanwhile a new basket is prepared and submerged in vessel V-6. This process is repeated in one week intervals with each basket being moved forward one vessel at a time until each vessel has a resident basket.

A commercial system using this system of operation can be designed based on the quantity of extract liquor required. For example, if 500 gallons of extract liquor is needed per week each of the vessels is sized so that its working capacity is 500 gallons. The manure baskets are sized proportionately based on a preferred 5 to 1 ratio of water to manure. Each basket is soaked for a period of one week. This continues at weekly intervals until all elements of the system have adequately aged and are producing extract liquor of high quality. At the end of six weeks all of the baskets will be active and extract liquor will be almost completely formed in the system. At the end of seven weeks five hundred gallons of liquor can be discharged from vessel V-6 and the system can again be brought up to operating level.

The system just described can be operated, continuously or semi-continuously depending on need. In a continuous operation approximately 3 gallons of fresh water per hour is added to the first vessel in the system. Each vessel is so arranged that overflow from the first vessel is discharged into the second vessel and so-on down the line to vessel V-6. The product from V-6 is passsed through filter 12 and then to storage tank 14. Each vessel is equipped with a recirculating pump 16 (FIG. 2) to insure that liquid is taken from the bottom of the vessel and recirculated over the manure in the basket. The liquid is discharged below the level of liquid in the basket so that atmospheric oxygen is not deliberately drawn into the system. Each of the recirculating systems can be provided with a small heater, not shown, to maintain the temperature between about 60 and 80 degrees Fahrenheit for optimizing the production of extract liquor and gas evolution As seen in FIG. 2 unfiltered extract can be drawn off into storage tank 18 until ready for final filtering. Filtered extract is stored in tank 20 for later distribution. Water is supplied by pump 24 through line 22 for cleaning filter 12.The backwash water is fed into the process via line 26 so as not to cause a waste stream from the facility. Valving 28 is used throughout the system to achieve the desired flow patterns.

The second ingredient of the mixture is molasses, a syrup produced in the refining of sugar. The effect of these sugar residues is quite well known as being beneficial materials to be fed animals or sprayed upon the soil to enrich it and the microbes which are present in the soil. It has been found that fire ants when wetted by either extract liquor or molasses, or both of these liquids in combination, will drown or suffocate when their bodies are thoroughly wetted. The extent to which fire ants are exterminated using this mix is on the order of 40 to 50% in a time period of several hours. Once the liquid is absorbed into the ground it has no further effect on the fire ant but does provide food for the microbial life of the soil and the plants.

The above two ingredients are assisted in their lethality to fire ants by the addition of a light paraffinic oil of the same chemical nature as oils used for laxatives but lower in molecular weight and of a narrower boiling range. It is also well known that petroleum oils are not soluble in aqueous systems such as described herein. The meaning to be ascribed to the term "paraffinic oil" as used in the specification and claims, is a paraffinic oil coming within the following specifications: A paraffinic oil is one having an API Gravity @ 60 degrees Fahrenheit of between 26 and 39, a viscosity of between about 60 and 130 SUS @ 100 degrees Fahrenheit, an unsulfonated residue minimum of 92%, a Pour Point of between about −20 and +130 degrees Fahrenheit and an ASTM 1160 distillation @ 760 mm Hg within the following ranges: (a) Minimum Boiling Range of between 525 to 625 degrees Fahrenheit; (b) 50% Boiling Point 650 to 775 degrees Fahrenheit; and (c) an End Point of between 750 to 875 degrees Fahrenheit. The preferred viscosity is between 70 and 100 SUS @ 100 degrees Fahrenheit. The accepted definition of a paraffinic oil as used herein is as follows: (1) The carbon content of the oil associated with an aromatic molecule is essentially zero, (2) The carbon content of the oil associated with a linear or branched paraffin is between about 60 and 70 percent and (3) The balance of the carbon content of the oil is associated with napththenic compounds which are saturated paraffins but have a ring structure. One such oil is Whitmire Micro-Gen Ultra-Fine Oil (US EPA Registration No. 862-23-499). Another such oil is ExxonMobile "EXXON DORMANT SPRAY OIL 100" (US EPA Registration No. 644-105). Either of these oils in the presence of oxygen and microbes will bio-degrade resulting in the typical products of decomposition, i.e. carbon dioxide and water. It also was found that the following oils were effective for use in fire ant pesticidal formulations: Castor Oil (U.S.P.), Corn Oil, Cottonseed Oil, Lemon Grass Oil, and Soybean Oil.

The composition composed of extract liquor, molasses and paraffinic oil is homogenized by addition of a detergent such as a soap or other non-ionic surfactant and mechanically blended as by use of a "Waring Blender". Surfactants are well known to be safe for contact with the skin, biodegradable and non-toxic. The surfactant, soap or other type emulsifier facilitates emulsification of the paraffinic oil into the total liquid phase of the system and in achieving the ultimate objective of providing a system which will result in the complete and almost instantaneous wetting of the fire ant and in its immediate demise.

The ultimate objectives in combining these materials was to achieve a low cost treatment which was simple in application, did not harm the surrounding vegetation or water supply, was ecologically benign and was an effective killer of fire ants in as few applications as possible. After extensive testing I found that a highly stable and most effective recipe for a four element concentrate comprised the following formulation and proportion of ingredients. Two gallons of extract liquor; eight fluid ounces of liquid soap, such as liquid Dove Soap; sixteen fluid ounces of paraffinic oil; and sixteen fluid ounces of molasses. The paraffinic oil in the systems tested contained a dispersing agent, usually a non-ionic, high molecular weight, alcohol. This mixture when dispersed with a mechanical dispersing machine, such as a blender, remained stable for about six months. This factor augers well for the wide-scale, and convenient containerized distribution of the concentrate in the war against the fire ant.

It will be recognized that there are other formulations involving differing proportions of the prescribed ingredients which will produce the desired end result of eradicating fire ants. However the above-described system is one such formulation which has been found to be highly effective in meeting the defined objectives in an expedient and economical manner. To demonstrate the versatility of the system it was found, for example, that the quantity of paraffinic oil, or the quantity of molasses, which can be used in the concentrate can be varied from one fluid ounce to sixteen fluid ounces per four gallons of the final concentrate solution without materially reducing the overall effectiveness of the concentrate.

By taking one quart of the preferred concentrate formulation as discussed above and diluting it with two gallons of water one has a very effective mixture for the eradication of fire ants. I have found that the final ratio of concentrate to water may vary from one volume of concentrate used alone to one volume of concentrate used with fifteen volumes of water and still be effective as a fire ant pesticide. Dilutions in excess of fifteen to one may be sprayed directly on green house plants to eliminate spider mites or mealy bugs or other commonly encountered green house bugs. The dilution ratio of one volume of concentrate to eight volumes of water was found to represent an optimum concentration for the elimination of fire ants.

Although a mixture at any of the above dilution ratios has a killing effect upon fire ants it should be noted that in using the more dilute systems it was necessary to treat older fire ant hills more times in order to eradicate the ant population. In instances where the hill has been recently "founded" the more dilute systems are extremely effective. The older the hill the more stable the population and the more difficult it is to kill the populations with dilution ratios greater than eight volumes of water per volume of concentrate.

While I have discovered that the above-described formulation of pesticide is the preferred and most effective means of eradicating fire ants I also found that certain sub combinations of the components making up the preferred concentrate formulation are to a lesser degree also effective. It was found, for example, that undiluted extract liquor used without the accoutrements of paraffinic oil, molasses, or surfactant was effective in killing fire ants. I also found that a mix of molasses and water could also be effective in killing fire ants using from one to sixteen fluid ounces of molasses in four gallons of water as a treatment solution. Other effective combinations are to use water, molasses, or water without molasses, a dispersant and an oil selected from one of the following: Castor Oil (U.S.P.), Corn Oil, Cottonseed Oil, Lemon Grass Oil, or Soybean Oil.

It will be appreciated that the size, shape and internal anatomy of a fire ant nest is dependent on soil type and vegetation. Some mounds reach heights and widths exceeding three feet. Its interior is riddled with galleries and chambers and a mirror image of the cone-shaped external edifice develops well below ground. Galleries and horizontally extending tunnels can occupy more than half the total volume of a mound. A preferred method of applying the solution to a fire ant mound is to take a probe, such as a 36 inch section of a broom handle, one end of which has been chamfered, and use it to drive a hole down into the main descending tunnel of the mound. By then pouring water down the hole until rapid drainage stops one can determine the approximate amount of solution which will be required to inundate the mound. If one pours one gallon of water into a hole and it disappears within about 30 seconds the drainage is considered rapid and the mound relatively small. As the drainage time decreases the size of the mound and the quantity of solution needed effectively to treat it is correspondingly greater. The average ant hill which I have treated took between two to three gallons of water before the mound was apparently filled; the liquid disappearing in about three to five minutes. This provides a good indication of the amount of solution which will be required to fill the mound effectively to eradicate the in-residence fire ants.

An example, using one quart of the concentrate diluted with two gallons of water, was to locate a fire ant hill. The hill which was located had an external mound of about five inches in diameter. When a hole was punched in the mound the probe penetrated about seven inches. It took about three quarts of the diluted concentrate to completely fill the hole and its radiating chambers and galleries. Five, ten and fifteen days after the above treatment there was no sign of ant activity. Similar treatment of an ant hill in which the probe went into the ground about 14 inches required the use of an additional gallon of the concentrate solution. After fifteen days there was no evidence of ant activity. Numerous fire ant hills were treated with similar results.

It will be understood that modifications of my preferred composition of concentrate differing from that which I have described but utilizing the basic components of my system can be devised without departing from the essential teaching of my discovery. Accordingly reference should be had to the appended claims rather than to the foregoing specification as defining the true scope of my invention and its equivalents.

I claim:

1. A biodegradable fire ant pesticidal emulsion consisting essential of water or extract liquor, a detergent, molasses, and one of the following oils: Paraffinic Oil; Castor Oil, Corn Oil; Cottonseed Oil; Lemon Grass Oil, or Soybean Oil.

2. A biodegradable fire ant pesticidal emulsion of water or extract liquor, a detergent, molasses, and one of the following oils: Paraffinic Oil; Castor Oil (USP); Corn Oil; Cottonseed Oil; Lemon Grass Oil; or Soybean Oil, having an optimum formulation substantially as follows per 128 volumes of final product: water or extract liquor between 117 and 84 volumes, molasses between 5 and 18 volumes, oil between 5 and 18 volumes, and detergent between one and eight volumes, the volumes of molasses and oil being essentially equal.

* * * * *